United States Patent [19]

Schmidt

[11] 4,194,127
[45] Mar. 18, 1980

[54] PROCESS AND DEVICE FOR CHECKING SUBSTRATE WAFERS

[75] Inventor: Walter Schmidt, Lenzburg, Switzerland

[73] Assignee: Swiss Aluminium Ltd., Chippis, Switzerland

[21] Appl. No.: 887,516

[22] Filed: Mar. 17, 1978

Related U.S. Application Data

[63] Continuation-in-part of Ser. No. 755,135, Dec. 29, 1976, abandoned.

[30] Foreign Application Priority Data

Jan. 20, 1976 [CH] Switzerland .......................... 625/76

[51] Int. Cl.² .......................................... G01N 21/32
[52] U.S. Cl. .................................. 250/572; 356/371; 356/445
[58] Field of Search .......................... 33/1 M; 250/572; 356/120, 209

[56] References Cited

U.S. PATENT DOCUMENTS

| 3,782,827 | 1/1974 | Niesenson et al. | 356/120 |
| 3,836,787 | 9/1974 | Ash | 250/572 |
| 4,017,188 | 4/1977 | Sawatari | 356/120 |
| 4,030,837 | 6/1977 | Kojima et al. | 356/209 |

Primary Examiner—James B. Mullins
Attorney, Agent, or Firm—Bachman and LaPointe

[57] ABSTRACT

Polished single crystal wafers are checked for defects by means of a method employing a optical microscope. The image is blurred by a translucent material and the transmitted light is then sensed by a light sensitive instrument which records the increased light intensity caused by a defect passing through the field of view. The position of the defects are then plotted automatically.

21 Claims, 2 Drawing Figures

PROCESS AND DEVICE FOR CHECKING SUBSTRATE WAFERS

CROSS-REFERENCES TO RELATED APPLICATIONS

This is a continuation-in-part application of application Ser. No. 755,135, abandoned, filed on Dec. 29, 1976.

BACKGROUND OF THE INVENTION

The invention relates to a process and device for checking substrate wafers, platelets or similar components which contain defects, and concerns in particular, a process and device for checking polished wafers of single crystal material with the aid of a microscope.

Platelets or wafers of single crystal materials, such as gallium-gadolinium garnet (GGG), are employed as the substrate in the epitaxial deposition of magnetic garnets. The required surface finish, however, can be achieved only by means of a very extensive polishing process in which the reproducibility of results does not depend finally on the concentration of dust particles, impurities in the polishing materials, or similar factors. The main difficulty usually lies in the presence of submicroscopic scratches which can not be seen, even at a magnification of several hundred times, without etching the surface.

The final examination of the wafers is a very important step in the whole manufacturing process. For this reason, both sides of the wafer are etched before inspection, since the defects become only then visible. The etched wafers are then usually examined for etch pits or scratches at magnifications of 100–200 times using incident light, and NORMARSKI microscopy, an optical inspection technique utilizing interference contrast. This manual inspection is very time-consuming since, at a magnification of two hundred times for example, only a very small area can be observed. Also, as is well known, microscopic observation of a moving field over a long period of time makes heavy demands on the viewer's concentration and is therefore extremely tiring.

Previous inventors have attempted to cope with this problem. For example Sawatari, U.S. Pat. No. 4,017,188, teaches an arrangement for measuring the profile of surfaces having a characteristic one-directional lay with sufficient resolution to determine the surface roughness. The surface is optically scanned with the aim of having a profile of the surface, i.e. a linear graphical profile of the surface is obtained by recording the signals as a function of the scanned distance.

Ash, U.S. Pat. No. 3,836,787, relates to apparatus for examining the surface of an object using electromagnetic radiation. The resolution is not limited by the wavelength of the radiation. The object has points to be determined which are smaller than the resolution of the apparatus. The surface of the object includes a plate having a small aperture in the centre of the field of view. The object must be vibrated relative to the plate having the aperture, so that radiation reflected from the object is modulated with the frequency of the vibration, namely the character of the reflected radiation differs from the character of the incident radiation.

Nisenson, U.S. Pat. No. 3,782,827, teaches an optical device which is useful for characterizing the surface topography of an opaque sample through the use of the sample's power spectrum, using light which is at least partially coherent. If one has none-opaque samples it is not possible to determine the morphology of the surface, but only variations of the refraction index.

Kojima et al., U.S. Pat. No. 4,030,837, teaches a method for measuring the reflectance of coals, including the provision of a movable sample stage below a microscope, and utilizing a combination of a microscope and photomultiplier. In converting the reflected light to an electrical output, Kojima integrates the electrical output.

The prior art thus discloses either an arrangement for measuring the profile of a surface by means of a light detector adapted only to measure the light distribution of light intensity without mapping point defects, as in Sawatari, requires an apparatus where the radiation from the reflected object must be different than the radiation incident on the object, as in Ash, characterizes properties of the sample through the uses of the sample's coherent power spectrum, as in Nisenson, or automatically measures the distribution of reflectance of coals, by integrating reflected light from a sample, and then indicates the distribution of reflectance, as in Kojima et al. None of the above references teach, however, a process for checking substrate wafers or the like for defects by optically sensing light differences between portions of an image free from defects, and portions of the image showing defects, and displaying the processed information in two dimensions on a display device.

Although attempts have been made in registering merely number of defects, there is no value, however, in registering only the number of defects, for example by counting the number of defects automatically, or otherwise, since their distribution is also very important. Consequently, a high local concentration of defects can be classified as a single defect when considering the extent to which the defects cause degeneration of the magnetic epitaxial layer.

SUMMARY OF THE INVENTION

Since a defect counting process, particularly a counting process carried out by an operator, is extremely time-consuming and tiring, one of the objects of the present invention is to develop a process and device, which avoids the above-mentioned difficulties.

In order to obtain a map of the defects present, two axes of movement of a microscope stage have been connected to linear transducers, or such devices which allow x-y coordinates to be transferred electronically onto a viewing surface. The movement of the microscope stage has been mechanized in such a way that the wafer is scanned in a regular manner. If the observer finds a defect while scanning he can, for example, record this on an x-y recorder, and thus obtain an enlarged plot of the number and distribution of the defects.

The process for checking substrate wafers, platelets or similar components containing defects, in particular for checking polished wafers of a single crystal material with the aid of a microscope thus includes the steps of moving the substrate wafer in two dimensions, optically sensing light differences between portions of an image on the substrate wafer free from defects, and between portions of the image showing defects, automatically transforming the light differences into electric signals, feeding the electric signals to a display device having an indicating element movable in synchronism with the movement of the substrate wafer and responsive to the electric signals, converting the electric signals into light, and displaying the information in the two dimensions on the display device.

The steps advantageously include substantially focusing light from a central part of the image from the substrate wafer, preferably through an aperture, onto dispersing means, such as ground glass, dispersing the selected light from the dispersing means, and impinging the dispersed light onto a light-to-electric current converter.

The light-to-electric current converter is preferably a photo-multiplier which is introduced into the light path of the microscope which operates by light reflection, light transmission, or a combination of both.

The light-to-electric current converter preferably includes an amplifier, and the steps further include increasing the current of the amplifier upon sensing the relatively lighter portions on the substrate wafer.

The steps preferably include contrast-selecting the electric signals, and amplifying the contrast-selected signals; it is also desirable to additionally frequency select the amplified signals.

Alternately, the steps may include frequency-selecting the electric signals, and subsequently amplifying the frequency-selected signals.

It is desirable if the electric signals have a plurality of levels, and the steps further include selecting the levels, and feeding the selected levels to the plotter directly.

The device of the present invention for use in checking a substrate wafer for defects includes in combination a microscope adapted for viewing a selected portion of the wafer, and for forming an image of the wafer, a transport device disposed in the vicinity of the microscope for selectively moving the wafer in two dimensions, a light-to-current converter disposed in the vicinity of the microscope for receiving light from the image of the wafer, for optically sensing light differences between portions of the image of the wafer free from defects, and between portions of the image showing defects, for automatically transforming the light differences into electrical signals, and a plotter connected to the light-to-electric current converter. The plotter has an indicating element, or pen connected to the transport device and may be moved in synchronization therewith; it is responsive to the electrical signals, so that a magnified image of the substrate wafer may be plotted on the plotter. The microscope is preferably formed as an aperture for viewing the selected portions of the image of the wafer, and the light from the image of the wafer may be passed through the aperture to the light-to-electric current converter. A display means other than a plotter can also be used. It has been found particularly favorable to insert between the microscope and the photo-multiplier at least one matt, translucent disc.

A light from a selected central region of the image is then scattered by the translucent disc or discs, which are preferably positioned on both sides of the aperture, and then passes into the photo-multiplier. The defects, as they appear in the microscope, are bright in contrast with the background, and therefore cause an increase in the photo-multiplier current on passing across the central field of view. If, in accordance with the invention, a slit-shaped aperture is used, then the width of the region examined per scan can be increased.

In accordance with another feature of the invention, at least one signal amplifier is provided in the circuit following the photo-amplifier; this amplifier is preferably a contrast-selecting amplifier, followed by a frequency-selective amplifier. Signal-drift problems can be avoided by inserting a capacitor in the transmission circuit, namely between the contrast-selective amplifier and the frequency-selective amplifier, the latter eliminating all background signals. It is preferable to include an electronic toggle switch or trigger means for the amplifiers. The trigger means preferably includes two triggers, the levels of which may be adjusted. It is possible to adjust the trigger devices so that only signals having a level between the first trigger level and the second trigger lever are further transmitted, so that the smallest signals and the signals having the largest levels can be excluded from transmission. By an appropriate choice of levels, it is also possible to select different defects.

From the triggers, there is preferably provided a comparator or comparison logic, which activates the indicating device or pen of the plotter only when the trigger for the lower level of registration provides a signal. If different impulses are provided from both the triggers, or neither of the triggers, then the pen or indicating device of the plotter does not move. The plotter is in turn connected to a control or transport device which guides the pen or indicating device within the examined field. This control unit or transport means is also connected to the microscope.

The device of the present invention has been found to be particularly useful in that it can operate without supervision, which means that it can operate also in the dark or during the night.

It is preferable if a wafer changer is disposed in the vicinity of the microscope for changing the wafer; such a wafer changer, which is preferably automatic, has been found to be very time-saving. In this fashion, a complete plot or map of defects of the whole wafer surface can be produced.

BRIEF DESCRIPTION OF THE DRAWINGS

For a fuller understanding of the nature and objects of the invention, reference should be had to the following detailed description taken in connection with the accompanying drawings in which.

DESCRIPTION OF THE PREFERRED EMBODIMENTS

Figure 1:
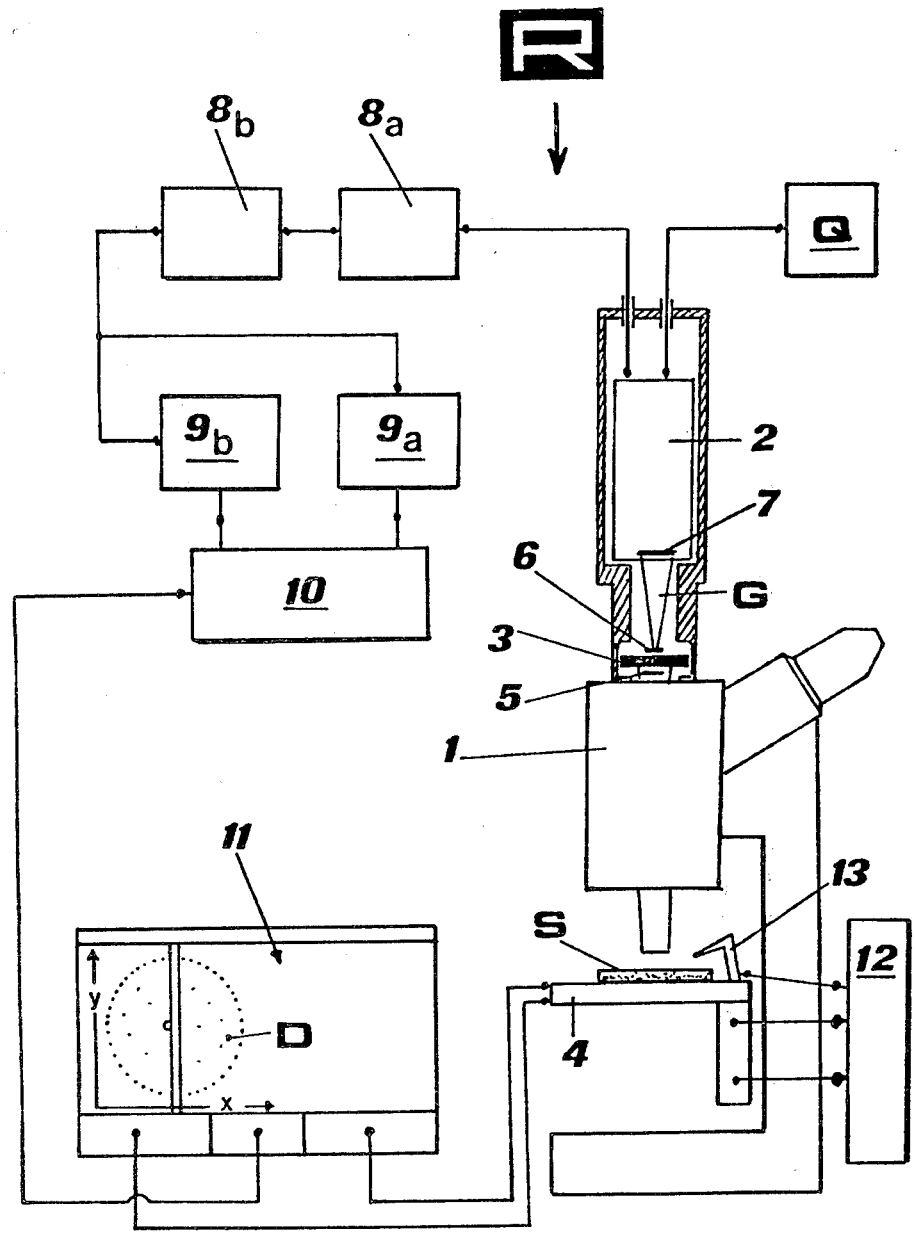
FIG. 1 shows a schematic representation of the device of the invention.

A highly sensitive photo-multiplier 2 is positioned on a microscope 1 in such a way that, by means of an aperture 3, only a small part or central area of the image of a wafer sample S on the microscope stage 4 is imaged. The light forming this selected part of the image is scattered by two matt, translucent discs 5, 6 positioned in a light path G of a device R, before entering the photo-multiplier 2 at its input window 7.

If the wafer S is now moved, its defects D, on passing through that central region being imaged, produce an increase in current in the photo-multiplier 2 which is connected to a high voltage source Q. The defects D appear light in the microscope 1, in contrast with the dark background, and therefore generate electric signals.

The photo-multiplier is connected to a contrast-selective amplifier 8a operating in a capacitive manner, which in turn is connected to a frequency-selective amplifier 8b. At the output side of the amplifier 8b, there are provided two triggers 9a and 9b, the actuating levels of which are set at different values.

Both triggers 9 are also connected to a comparator 10, which in turn is connected to a plotting device 11, the pen of which is not shown in detail here, and which is actuated by the comparator 10 as soon as the comparator 10 receives a signal which reaches the actuating level of the trigger set at the lower signal value.

A device 12 controls the movement of the imaged region in the x and y directions. This also actuates an automatic sample changer 13 on the microscope stage 4.

Figure 2:
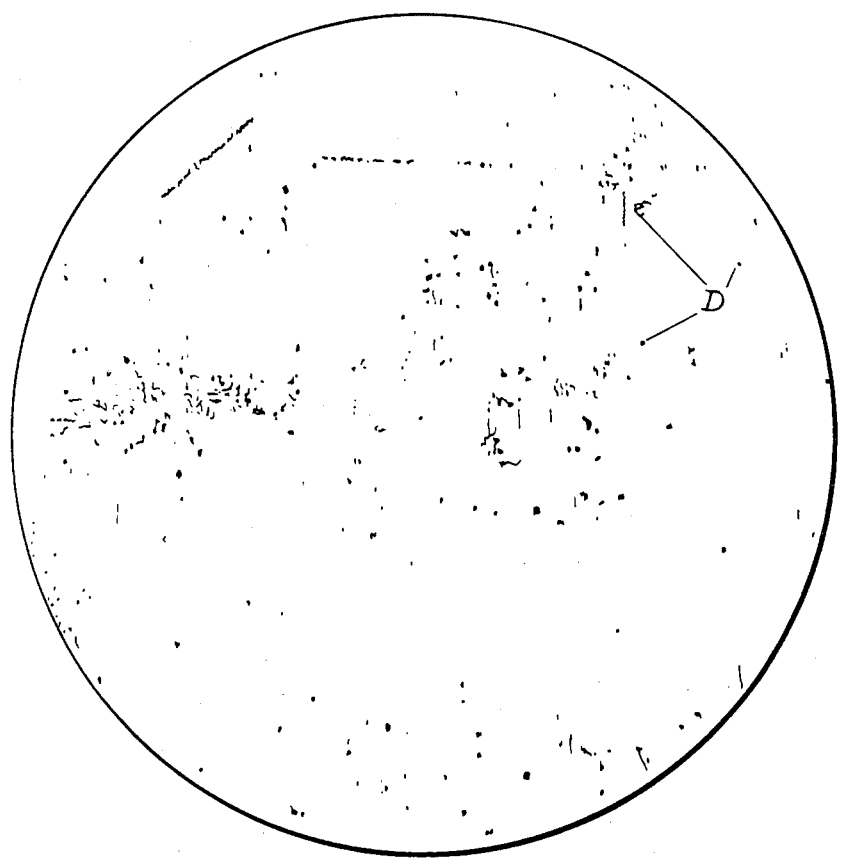
FIG. 2 shows a plot of the defects at an enlargement of five times the wafer size, although the defects themselves are detected at a magnification of several hundred times.

The map of defects (D) on the plotting device II shown in FIG. 1, is enlarged in FIG. 2 to its normal size, to make it clearer.

I wish it to be understood that I do not desire to be limited to the exact details of construction shown and described, for obvious modifications will occur to a person skilled in the art.

Having thus described the invention, what I claim as new and desire to be secured by Letters Patent is as follows:

1. A method for determining the number and distribution of defects in substrate wafers, particularly polished wafers of single crystal materials comprising:
   moving said wafer in two dimensions;
   projecting light on said wafer;
   conducting light reflected by said wafer to a photosensor;
   sensing the intensities of said light reflected by said wafer;
   transforming the differences of said sensed light intensities into an electrical signal;
   feeding said signal to an indicating element responsive to the strength of said electrical signal; and
   moving said indicating element in synchronism with said wafer whereby the number and distribution of defects on said wafer are displayed by said indicating element.

2. The method of claim 1 further including
   providing a movable stage below a microscope;
   locating said wafer on said stage;
   stepwise moving said stage in two dimensions; and
   conducting said reflected light to said photosensor via said microscope.

3. The method of claim 1 further including
   focusing said reflected light onto dispersing means;
   dispersing the selected light from the dispersing means; and
   impinging the dispersed light onto a light-to-electric current converter.

4. In a process according to claim 3 wherein the light-to-electric current converter includes amplifier means, the steps further comprising increasing the current of the amplifier means upon sensing relatively lighter portions on the substrate wafer.

5. In a process according to claim 1, the steps further comprising contrast-selecting the electric signals, and amplifying the contrast-selected signals.

6. In a process according to claim 5, the steps further comprising frequency-selecting the amplified signals.

7. In a process according to claim 1, the steps further comprising frequency-selecting the electric signals, and amplifying the frequency-selected signals.

8. In a process according to claim 1, wherein the electric signals have a plurality of levels, the steps further comprising selecting the levels, and feeding the selected levels to the plotter.

9. A device for use in checking a substrate wafer for defects, comprising, in combination:
   a microscope adapted for viewing a selected portion of the wafer and for forming an image of the wafer;
   transport means disposed in the vicinity of said microscope for selectively moving the wafer in two dimensions;
   a light-to-electric converter disposed in the vicinity of said microscope for receiving light from the image of the wafer, for optically sensing light differences between portions of the image of the wafer free from defects, and between portions of the image showing defects, and for automatically transforming the light differences into electric signals; and
   display means connected to said light-to-electric current converter, said display means having an indicating element connected to said transport means, being movable in synchronism therewith, and being responsive to the electric signals, whereby a magnified image of the substrate wafer is displayable on said display means whereby the number and distribution of defects on said wafer are displayed by said indicating element.

10. A device according to claim 9, wherein said microscope is formed with an aperture for viewing the selected portion of the image of the wafer, the light from the image of the wafer being passable through said aperture to said light-to-electric current converter.

11. A device according to claim 10, further comprising at least one matt and translucent disc disposed on each side of said aperture.

12. A device according to claim 10, wherein said aperture is slit-shaped.

13. A device according to claim 9, further comprising an amplifier connected to said light-to-electric current converter for amplifying the electric signals.

14. A devide according to claim 13, further comprising a contrast-selective amplifier which includes a capacitor, said amplifier and said capacitor being interconnected between said light-to-electric current converter and said display means.

15. A device according to claim 14, further comprising a frequency-selective amplifier interconnected between the contrast-selective amplifier and said display means.

16. A device according to claim 14, further comprising triggering means interconnected between said frequency-selective amplifier and said display means.

17. A device according to claim 16, wherein said triggering means comprise first and second trigger amplifiers having different respective signal actuating levels.

18. A device according to claim 16, further comprising a comparator interconnected between said light-to-electric converter and said display means, said indicating element being actuatable by said comparator upon receiving a signal-actuating level from one of said trigger amplifiers.

19. A device according to claim 18, wherein said one of said trigger amplifiers has a signal-actuating level lower than the other signal-actuating level.

20. A device according to claim 9, further comprising wafer change means disposed in the vicinity of said microscope for changing the wafer.

21. A device according to claim 9, wherein said display means includes a plotter.

* * * * *

UNITED STATES PATENT AND TRADEMARK OFFICE
CERTIFICATE OF CORRECTION

PATENT NO. : 4,194,127
DATED : March 18, 1980
INVENTOR(S) : Walter Schmidt

It is certified that error appears in the above-identified patent and that said Letters Patent are hereby corrected as shown below:

Column 4, line 11, change "lever" to --level--.

Column 6, line 39, Claim 14, change "devide" to --device--.

Signed and Sealed this

Nineteenth Day of August 1980

[SEAL]

Attest:

SIDNEY A. DIAMOND

Attesting Officer     Commissioner of Patents and Trademarks